United States Patent [19]

Shah et al.

[11] Patent Number: 4,624,916

[45] Date of Patent: Nov. 25, 1986

[54] PROCESS AND COMPOSITION FOR THE RAPID QUANTITATION OF SMALL LEVELS OF CREATIVE KINASE-MB ISOENZYME

[75] Inventors: Vipin D. Shah; Nila V. Shah, both of Saratoga, Calif.

[73] Assignee: International Immunoassay Laboratories, Inc., Santa Clara, Calif.

[21] Appl. No.: 597,593

[22] Filed: Apr. 6, 1984

[51] Int. Cl.⁴ .................. A61K 39/00; G01N 33/53
[52] U.S. Cl. .......................... 435/7; 424/85; 435/17; 435/810; 436/524; 436/525; 436/526; 436/527; 436/528; 436/529; 436/530; 436/531; 436/532; 436/533; 436/534; 436/547; 436/808; 436/811; 436/825; 436/826; 530/387; 530/389; 530/402
[58] Field of Search ............ 435/7, 17, 810; 436/524–535, 547, 808, 811, 825, 826; 424/85; 530/387, 389, 402

[56] References Cited

U.S. PATENT DOCUMENTS

| | | | |
|---|---|---|---|
| 3,852,415 | 12/1974 | Vandervoorde | 436/813 X |
| 4,012,285 | 3/1977 | Pfleiderer et al. | 436/811 X |
| 4,020,151 | 4/1977 | Bolz et al. | 436/825 X |
| 4,067,775 | 1/1978 | Wurzburg et al. | 436/811 X |
| 4,260,678 | 4/1981 | Lepp et al. | 435/7 |
| 4,267,271 | 5/1981 | Roberts | 435/7 |
| 4,298,592 | 11/1981 | Lin et al. | 436/540 |
| 4,353,982 | 10/1982 | Gomez | 435/7 |
| 4,414,324 | 11/1983 | Stout | 435/7 |

FOREIGN PATENT DOCUMENTS

| | | | |
|---|---|---|---|
| 2026156 | 1/1980 | United Kingdom | 435/7 |
| 2093182 | 8/1982 | United Kingdom | 435/7 |

OTHER PUBLICATIONS

Biagini et al., from *Radioimmunoassay of Drugs and Hormones in Cardiovascular Medicine*, Albertini et al., Eds., Elsevier/North Holland Biomedical Press, Amsterdam, 1979, pp. 85–92.

*Primary Examiner*—Christine M. Nucker
*Attorney, Agent, or Firm*—Hamrick, Hoffman, Guillot & Kazubowski

[57] ABSTRACT

A process for conducting fast, rapid two site, two step immunoradiometric tests for CK-MB.

In a first series of steps, a mobile particulate solid-phase having an isoenzyme selected from the group of CK-BB and CK-MM immobilying bound on its surface is suspended in a matrix of pooled match human serum. The mixture is incubated, diluted, and centrifuged.

In a second series of steps, the resulting solid is incubated with a radio labeled antibody that is specific to the isoenzyme not used in the first series of steps. Counting the radioactivity gives the amount of CK-MB in the patients serum.

16 Claims, No Drawings

PROCESS AND COMPOSITION FOR THE RAPID QUANTITATION OF SMALL LEVELS OF CREATIVE KINASE-MB ISOENZYME

BACKGROUND OF THE INVENTION

1. Field of the Invention

The present invention relates generally to immunological assay techniques for determining the presence of an analyte in serum. More particularly, this invention relates to processes that are useful in determining very small elevations of CK-MB in patients who have experienced acute myocardial infarction.

2. Description of the Prior Art

Creatine Kinase (hereinafter CK) occurs in animal body fluids and tissues in several forms including isoenzymes CK-MM, CK-BB, CK-MB, CK-BB.IgG, Mitochondrial CK and other short lived variants of CK-MM and CK-MB. While the exact structures of some of these isoenzymes have not been identified, it is clear that each of them includes two of the subunits of CK, the B subunit and the M subunit. The level of circulating CK-MB has proved to be the most reliable indicator myocardial damage, and the level of CK-MB in circulating blood increases when the necrosis of mycardial cells rich in CK-MB occurs.

Several methods, including both immunological and non-immunological methods, have been described for measuring CK-MB levels. Many of these methods such as electrophoresis, column chromatography, immunoinhibition, and B-unit radioimmunoassay (hereinafter RIA) have not been satisfactory in providing the accurate and rapid measurement of CK-MB which is essential for immediate treatment of patients suffering from life threatening episodes of Acute Myocardial Infarction (hereinafter AMI). It is estimated that an accurate detection of one to two nanograms (ng) per milliliter (ml) increase in the level of CK-MB in the patients blood is required to make the earliest possible diagnosis of AMI. Typically, when the analytical sensitivity of a CK-MB test method is increased in an attempt to measure such small elevation, the specifically is decreased due to the interference from isoenzymes of CK other than CK-MB and other non-specific effects. The inaccuracy in measurement of the small elevations of circulating CK-MB, so essential for accurate diagnosis of AMI is caused by the limitations of specifically and sensitivity.

The difficulties encountered in accurately measuring small elevations CK-MB by non-immunological methods arise due to poor separation and recovery of the CK-MB isoenzymes in specimens that contain several forms of CK. The non-immunological methods are based on the measurements of enzymatic activity of CK and require the separation of the CK-MB from other isoenzymes. These methods include electrophoresis or column chromatography and are described in U.S. Pat. Nos. 4,105,499; and 4,046,634. They produce inaccurate results due to low sensitivity, incomplete separation, poor analytical recovery, and artifacts. The selective activation procedure, described in U.S. Pat. No. 3,994,783, was a non-immunological procedure not requiring separation. However, it was quickly determined that the method did not have the sensitivity and accuracy required for clinical use.

Immunological methods are difficult to use because antibodies that are raised specifically against CK-MB cross react with other isoenzymes of CK due to the presence of either a B subunit or an M subunit in those isoenzymes. Yet, several immunological methods have been introduced as an attempt to increase sensitivity and specificity of the CK-MB measurement by utilizing antibodies raised against either CK-MM or CK-BB. Techniques based on the use of only one of these antibodies, specific for either the B subunit or the M subunit, were initially introduced as described in U.S. Pat. Nos. 4,067,775; 4,012,285; 3,932,221; and as described in an article by R. Roberts, et al. in The Lancet 319 (1977). These methods were found to measure other isoenzymes of CK besides CK-MB and found to produce erroneous results. Physicians who use these methods are therefore required to exercise great care when using these methods for the diagnosis of AMI.

Several new "sandwich" approaches have been proposed to overcome the problems encountered due to interference from other CK isoenzymes when antibodies specific to CK-MB or antibodies specific to only CK-MM or CK-BB are used. U.S. Pat. No. 4,353,982 describes a triple antibody technique for measuring CK-MB. In such a method, one unlabeled antibody reacts with one subunit of CK-MB, for example, the M subunit. The other antibody, that is labeled with a signal generating molecule, reacts with the second subunit of CK-MB, in thise case, the B subunit, forming a sandwich around CK-MB. CK-MB bound to the unlabeled antibody described above is precipitated from the reaction mixture by a third antibody, which is specifically formed against the IgG of the animal species used to make the unlabeled antibody. It has been shown that this technique is still prone to unacceptable interference from the other isoenzymes of CK in clinical situations, if the reaction is carried out in one step.

A two step method including precipitating the unlabeled antibodies after reaction with the specimen and diluting the undesirable impurities through the use of a wash liquid has been described in the copending commonly assigned patent application U.S. Ser. No. 165,001. The method involves a two-site sandwich technique which uses two cross-reactive antibodies in a two step procedure. This method has proved to be very accurate, and a test kit incorporating this method has been on sale in the United States for more than three years. Recently a one step method for utilizing two monoclonal antibodies raised against CK-BB and CK-MM and using immunoenzymatic labeling has been commercialized; this is the "Tandem CK-MB" test by Hybritech, Inc.

Immunometric methods using two polyclonal antibodies and two steps, such as is described in U.S. patent application Ser. No. 165,001, have eliminated many of the interference problems resulting from the other isoenzymes of CK. However, the procedures are lengthy requiring upwards to two to three hours to perform if one wants to detect small elevations of CK-MB accurately. In addition, non-specific reactions resulting from the use of iodinated tracers, and mobile particulate solid-phases, and intereference from other components present in the reaction mixture were found to occur, resulting in erroneous values. The immunoenyzomatic method using two monoclonal antibodies is also lengthy and was found to have interference with CK-BB.IgG.

It has recently become apparent that many of the patients who suffer AMI, and are at higher risk of mortality, have only a small increase in CK-MB. They are also generally more difficult to diagnose by other techniques such as electrocardiography. Many of these patients, if correctly diagnosed, could benefit from aggressive treatment involving open-heart surgery, administration of thrombolytic drugs or balloon catheterization. Thus, a need exists for accurate tests for CK-MB which could rapidly detect a small elevation of CK-MB.

The present invention is generally useful for all patients but is specifically aimed at rapidly and accurately detecting the small elevations of CK-MB indicative of AMI. In the instant invention a two-site two step immunoradiometric procedure for CK-MB is used in conjunction with a novel process and novel composition. The invention greatly increases the specific response due to CK-MB and simultaneously reduces non-specific reactions resulting from the tracer or sample matrix.

SUMMARY OF THE PRESENT INVENTION

The present invention provides suitable processing compositions whereby a two-site two step immunoradiometric prcedure for CK-MB as described in U.S. Pat. No. 4,353,982 or pending application U.S. Ser. No. 165,001 can be rapidly performed while increasing the sensitivity and specificity of such methods. The false positive results arising from non-specific reactions including those which can be eliminated through the use of serum albumin and non-ionic surfactants are essentially eliminated.

The present invention comprises a novel matrix including a particulate solid phase on which one of the two CK specific antibodies has been immobilized. The solid phase is surrounded by a liquid solution including matched healthy human serum. Preferably, the matrix also contains bovine serum albumin and human immunoglobulin (hereinafter IgG) and Polyethylene Glycol (hereinafter PEG). The matrix is utilized in a two step sandwich reaction. In a first step, patient serum is incubated with the matrix. After incubation the reaction mixture is diluted with a volume of liquid so that the particulate solid phase is diluted approximately 10 fold or more. The reaction mixture is then centrifuged and the solid phase is removed. In a second step, the resulting centrifuged solid is incubated with a minimum volume of $^{125}I$ labeled antibody which is specific to the other subunit of CK-MB than that used for the first step. Prior to utilization, the labeled antibody has been aged and filtered in the presence of an anion exchange resin. The second reaction mixture is diluted with a volume of liquid so that the particulate solid-phase is diluted approximately 10 fold or more and the second reaction mixture is then centrifuged.

It is preferred that the volume of the matched human serum used in the matrix range from 10 to 100% of the volume of the specimen. It is preferred that the volume of human IgG in the matrix be in the range of approximately 0.5 of the final matrix volume, and the amount of PEG be less than 7% of the final matrix volume of the particulate solid phase. It is preferable that the aging of the labeled antibody used in second reaction mixture range from three hours to four days, during which aging it is maintained at a temperature in the range of between approximately 0 degrees C to about 6 degrees C which facilitates the insolubilization of the undesirable by-products present in the tracer. The tracer also includes PEG and animal proteins.

DETAILED DESCRIPTION OF THE PREFERRED EMBODIMENT

Solid-phase immunoassay techniques have been used to enhance the accuracy and ease with which immunological tests could be performed. Mobile particulate materials made of for example, of latex, agarose, nylon, cellulose, polyvinylidena fluoride, polymeric membranes, as well as test tubes, cuvettes, and the like, have long been used as solid phase supports. One of the reactants of the immunological reaction is either physically or chemically attached to the solid phase material. The solid-phase immobilized reactant as used in a one-step or mutiple step immunoassay utilizing one of the following techniques; competitive binding, sequential binding, or sandwiching. The solid-phase assay techniques are easy to perform, but they have two major shortcomings. Many solid phase systems provide a surface on which undesired, non-specific reactions may occur. They may also hinder the rate at, and the extent to which, the immunological reaction occurs.

The rate that the solid-phase reaction occurs can be accelerated by increasing the surface area of the solid-phase by using mobile particulate materials or microbeads such as those made of latex, nylon, polyacrylamide, cellulose, and agrarose. However, the increased surface exposure required to increase the reaction rate also increases the non-specific binding, which may vary from sample to sample and varies due to different polymeric substrates. These problems become more severe when one wants to measure extremely low levels of an analyte rapidly, to make the results immediately available for critical decisions.

Conventionally, serum albumin and non-ionic surfactants, high salt concentrations, ethylene diamine tetracetate (hereinafter EDTA) and PEG have been added to the mobile solid phase to minimize such non-specific reactions and increase the rate of reaction. Usually, a large volume of dilutant is added prior to centrifugation to remove loosely bound materials which cause non-specific intereference.

With regard to RIA tracers, it is well known that ratioisotope labeled analyte undergoes some changes on aging, resulting in the flattening of the response curve. Often, the by-products of the deteriorating labeled antibody react with the particulate solid-phase causing the elevation of bound radioactivity and producing erroneously high values. Animal serum or serum albumins are often added to radiolabeled substances to minimize this interference. Simultaneously, substances like PEG, serum albumin, and non-ionic surfactants may be added to increase the reaction rate. The liquid that is used as a wash or diluent is often formulated with heat inactivated serums or non-ionic surfactants to minimize the non-specific reactions resulting from deteriorated tracers.

PEG or similar polymers are commonly used to accelerate antigen-antibody reactions, and PEG concentrations of up to 5% are often recommended. However, some IgG, IgM and other constituents are known to precipitate out when the PEG concentration is greater than 2.5%. Such precipitation will cause elevated values when $^{125}I$ labeled antibody is used for the test.

The present invention provides a suitable processing composition, whereby a two-site two step immunoradiometric procedure for CK-MB as described in U.S. Pat. No. 4,353,982 or pending application U.S. Ser. No. 165,001 can be rapidly performed while increasing the sensitivity and specificity of such methods. The false positive results arising from non-specific reactions including those which can be eliminated through the use of serum albumin and non-ionic surfactants are essentially eliminated.

It is difficult to conveniently measure a low level of analyte when the non-specific reactions occurring in the presence of the patients sample are greatly different from the non-specific reactions occurring in the presence of the serum used to make calibration samples. Such differences are known to generate false values. The same phenomenon is observed in the two-site two step mobile solid phase immunoradiometric test for CK-MB described in the copending U.S. patent application Ser. No. 165,001. It has been discovered however, that this difference is greately diminished if the calibration serum is also added to the mobile solid phase matrix utilized to test patient sample. The addition of the calibration serum minimizes the variation of the non-specific reaction resulting from variations in patient samples.

CK-MB is a unique analyte because it is generally absent, or present only in very small amounts over a very narrow range, in healthy individuals and because CK-MB is not known to bind to other serum constituents such as proteins. These characteristics allow one to add CK-MB free human serum to the mobile solid phase solution matrix to reduce the non-specific reaction effects. Therefore, the same human serum that is used to make calibrations for determining the level of CK-MB in the immunoassay can be added to the mobile solid phase matrix for the patient sample to reduce the non-specific binding effects. This serum is hereinafter referred to as "matched human serum" in that the human serum used in the patient sample matrix "matches" the human serum used to make the calibrators. The matched human serum is taken from a pooled human serum in order to provide a basic serum similar to most patient specimens. Serum from many individuals made into one batch is referred to as "pooled human serum". It has been observed that when matched human serum is used in conjunction with bovine serum albumin and human gammaglobulin, the non-specific reactions are greatly reduced in a two-site two step immunoradiometric assay for CK-MB. Addition of the matched serum to the mobile solid phase does not interfere with the measurement of CK-MB, because low levels of CK-BB, CK-BB.IgG and CK-MM and the other constituents present in the serum added to the solid phase do not interfere in two-site two step assays.

The two-site two step mobile solid phase assay of the present invention uses $^{125}I$ labeled antibody, although other types of labels could be conveniently utilized. Antibodies used for purposes of labeling are purified prior to iodination and are also purified after iodination. As a result, antibody based tracers consist mainly of high molecular weight proteins such as IgG and IgM. It has been observed that some of the high molecular weight proteins tended to non-specifically bind to the mobile solid phase. They also tended to precipitate out of solution upon aging and and could be removed by filtration. Thus, aging, followed by filtration greatly reduces the non-specific binding and enhances the sensitivity of the assay.

EXAMPLES

A test procedure to determine the effectiveness of the solid phase matrix of the present invention was conducted with calibrators having known concentrations of CK-MB that were analyzed along with unknown specimens. The abnormally elevated level of CK-MB is taken to be that level which is two standard deviations greater than the mean value obtained with specimens of patients suspected of AMI but which have been found not to have AMI. Clinical experience with the two-site two step assays for CK-MB indicates that non-AMI patients do not experience greater than approximately one to two ng/ml elevation of CK-MB during the chest pain episode.

REAGENTS USED

The Examples were run using the following reagents.

MOBILE PHASE

Commercially available mobile solid phase suspensions (LIMA Beads, Organon Corp., ElMonte, Calif.; Ab-SORB, AMF Corp., Segunin, Tex.) on which goat anti-rabbit IgG was attached by covalent linkage. Antisera raised in rabbit against human CK-BB isoenzyme was diluted and mixed with the mobile solid phase suspension. This suspension is referred to as Suspension A.

Bovine serum albumin (5%) and Tween 20 (0.5%) were added to Suspension A. This suspension is called Suspension B. Tween 20 is a well known name for Polyoxyethylenesorbitan.

Base (unclarified) human serum (20%), taken from the same pooled human serum from which the test calibrators are produced, and PEG (3%) and human IgG (0.5%) were added to Suspension B. This suspension is referred to as Suspension C. Suspension C is the matrix of the present invention.

TRACERS

Antibodies against human CK-MM were raised in goat. This antisera was affinity purified with human CK-MM and was used for labeling with $^{125}I$. The labeled antibody was purified over sephadex G-25 column and fractions IgG were pooled. This pool was diluted with phosphate buffer, saline solution at pH of approximately 7.5 containing 10% heat actived bovine serum. This material is referred to as Tracer D.

Tracer D was allowed to stand between 0 and 6 degrees C a refrigerator overnight. It was filtered in the presence of an anion-exchange resin (DOW-X). This tracer is referred to as Tracer E.

PEG (1–5%) was added to Tracer E with optional amounts of human IgG (0.5%) and Tween 20 (0.5%). This solution is referred to as Tracer F.

TEST PROCEDURE

The test procedure included two steps.

Step 1.—X microliters of sample was incubated with Y microliters of a mobile solid phase. This reaction was incubated at room temperature for M minutes and after the incubation, V milliliters of wash buffer was added and the tube was centrifuged for 10 minutes at a speed high enough to make a pellet. Such speed is about 1500 R.P.M. on a standard centrifuge. The supernatant was removed and the tubes were shaken to loosen the pellet.

Step 2.—Z microliters of tracer containing T total counts per minute was added to the tube and incubated for M minutes. After incubation W milliliters of wash liquid was added and the tubes were centrifuged as in step 1. The bound count was measured on a gamma counter.

ANALYSIS OF RESULTS

The effect of the matrix on increasing the specific response and decreasing the non-specific response was judged by an absolute value of ratio R where:

$$R = \frac{\% B/T_{CK} - \% B/T_{BS}}{\% B/T_{H_2O} - \% B/T_{BS}}, \text{ where:}$$

% B/T equals the ratio of bound count to total count; subscript CK refers to the sample containing four nonogram per milliliter CK-MB (or 2 U/L measured at 30 degrees celcius);

BS refers to the base serum which was pooled unclarified serum of healthy individuals; and $H_2O$ refers to distilled water used as a specimen. The absolute value of ratio R, when it is less than 1.5, reflects the situation in which the non-specific response was so high as to cause erroneous positive results. In general, the ratio decreases as the tracer ages, as time of incubation used for the test is decreased, and as the non-specific interference is increased.

The following comparative examples show how the conventional matrix containing serum albumin and a non-ionic surfactant gave undesirable values of R and how these values were increased through the use of the matrix of the present invention. Comparative data of the actual patients samples is provided to show that this novel matrix aided the test which could be run in less than hour. This test provided more reliable results than conventional procedures which need between 2.5 and 3 hours to perform.

The specific reaction to CK-MB was measured by using serum patients with confirmed AMI or obtained by adding purified human CK-MB to the human serum. The non-specific reaction to CK-BB and CK-MM was measured by adding purified human CK-BB and CK-MM into base serum. The non-specific reaction due to the matrix effect was measured by adding distilled water instead of the serum sample.

EXAMPLE 1

Table 1 shows the effect obtained with the new matrix mobile solid phase. All values in the Tables identified by letters are as previously defined.

TABLE I

Materials Added to the Matrix Containing Mobile Solid-Phase and Antibody to CK-BB (Suspension A)

| | | Matrix Type | | |
| --- | --- | --- | --- | --- |
| None | 5% BSA | 20% Matched Human Serum | 0.5% Human Gamma Globulin | All of Them |
| | | Tracer Type | | |
| E | E | E | E | E |

Test Protocol

| | | | | |
| --- | --- | --- | --- | --- |
| X, ul | 100 | 100 | 100 | 100 | 100 |
| Y, ul | 100 | 100 | 100 | 100 | 100 |
| M, Min | 60 | 60 | 60 | 60 | 60 |
| V, ml | 2 | 2 | 2 | 2 | 2 |
| Z, ul | 100 | 100 | 100 | 100 | 100 |
| N, Min | 60 | 60 | 60 | 60 | 60 |
| W, ml | 2 | 2 | 2 | 2 | 2 |

Results

| | | | | | |
| --- | --- | --- | --- | --- | --- |
| [% B/T] CK | 4.5 | 4.3 | 4.5 | 4.5 | 4.3 |
| [% B/T] BS | 3.5 | 2.6 | 2.9 | 2.8 | 2.3 |
| [% B/T] $H_2O$ | 3.9 | 3.7 | 3.4 | 2.9 | 2.7 |

TABLE I-continued

Materials Added to the Matrix Containing Mobile Solid-Phase and Antibody to CK-BB (Suspension A)

| | | Matrix Type | | |
| --- | --- | --- | --- | --- |
| None | 5% BSA | 20% Matched Human Serum | 0.5% Human Gamma Globulin | All of Them |
| | | Tracer Type | | |
| E | E | E | E | E |
| R  2.5 | 1.5 | 3.2 | 17 | 5 |

The results in Table 1 show that the combination of BSA, human serum and human gamma globulin reduced [% B/T] values for the serum and water and gave good discrimination between the sample containing four ng/ml more of CK-MB compared to the non-AMI serum pool.

EXAMPLE 2

Example 2 shows the impact of using the tracer of the present invention. One day old tracer solution containing animal protein which was not filtered was compared to the filtered tracer solution and the filtered tracer solution with the solid phase matrix of the present invention.

This example shows increased accuracy with the tracer made per the present invention.

TABLE II

| | Mobile Solid-Phase Type | | |
| --- | --- | --- | --- |
| | C | C | C |
| | | Tracer Type | |
| | D (unfiltered) | E (filtered) | F (filtered with matrix) |
| Test Protocol | | | |
| X, ul | 200 | 200 | 200 |
| Y, ul | 200 | 200 | 200 |
| M, Min | 60 | 60 | 60 |
| V, ml | 2 | 2 | 2 |
| Z, ul | 100 | 100 | 100 |
| N, Min | 60 | 60 | 60 |
| W, ml | 2 | 2 | 2 |
| Results | | | |
| [% B/T] CK | 4.9 | 4.5 | 7.8 |
| [% B/T] BS | 2.7 | 2.4 | 3.7 |
| [% B/T] $H_2O$ | 3.5 | 2.7 | 3.9 |
| R | 2.7 | 7 | 20.5 |

The data of Table II shows that PEG in the tracer solution increases the value of [% B/T] BS. However, the relative increase for the specific reaction was relatively higher than that for the non-specific reaction. This produced an increasing value for R.

EXAMPLE 3

This example shows that the incubation times could be reduced with mobile solid-phase and tracer made according to the present invention. It shows that when the mobile solid-phase matrix of the present invention is used, one could decrease the incubation time by more than 50% and still obtain accurate performance.

This example shows that the test per the present invention is more accurate than the conventional matrix even with the shortened incubation time of 30 minutes compared to sixty minutes for each incubation step.

TABLE III

| | Mobile Solid-Phase Type | | |
|---|---|---|---|
| | A | C | C |
| | Tracer Type | | |
| | E | F | F |
| Test Protocol | | | |
| X, ul | 200 | 200 | 200 |
| Y, ul | 100 | 100 | 100 |
| M, Min | 60 | 60 | 30 |
| V, ml | 2 | 2 | 2 |
| Z, ul | 100 | 100 | 100 |
| N, Min | 60 | 60 | 30 |
| W, ml | 2 | 2 | 2 |
| Results | | | |
| [% B/T] CK | 4.6 | 7.8 | 5.1 |
| [% B/T] BS | 2.9 | 3.7 | 3.3 |
| [% B/T] H$_2$O | 3.3 | 3.9 | 3.1 |
| R | 4.2 | 20.5 | 9 |

EXAMPLE 4

This example shows the effect of changing the volume of the mobile solid-phase matrix and the tracer solution.

TABLE IV

| | Mobile Solid-Phase Type | | | | |
|---|---|---|---|---|---|
| | C | C | C | C | C |
| | Tracer Type | | | | |
| | F | F | F | F | F |
| Test Protocol | | | | | |
| X, ul | 200 | 200 | 200 | 200 | 200 |
| Y, ul | 100 | 200 | 200 | 200 | 200 |
| M, Min | 30 | 30 | 20 | 20 | 20 |
| V, ml | 2 | 2 | 2 | 2 | 2 |
| Z, ul | 100 | 100 | 100 | 75 | 50 |
| N, Min | 30 | 30 | 20 | 20 | 20 |
| W, ml | 2 | 2 | 2 | 2 | 2 |
| Results | | | | | |
| [% B/T] CK | 4.6 | 7.8 | 5.1 | | |
| [% B/T] BS | 2.9 | 3.7 | 3.3 | | |
| [% B/T] H$_2$O | 3.3 | 3.9 | 3.1 | | |
| R | 4.2 | 20.5 | 9 | | |

The results of Table IV show that the accuracy and speed with which the assay could be performed could be changed by changing the volume of the mobile solid phase and tracer. One would expect to cause similar changes by increasing the concentration of the solid phase and/or immobilized antibody and also changing the amount of the specific radioactivity and concentration of the antibody used in the tracer.

Similar experiments were conducted to determine the effect of changing the amounts of bovine serum albumin. It was observed that the BSA concentration in the 1–10% range did not significantly affect the assay performance. The level of 5% BSA was used for most of this work.

The rate at which the reaction took place increased as the PEG concentration was increased from 0 to 7%. The [% B/T] BS values for non-AMI serum pool also increased as the PEG concentration was increased. Beyond 7% PEG, the solution containing $^{125}$I-labelled antibody become turbid suggesting that further addition of the PEG may precipitate out some of the labelled antibodies. A PEG concentration of 3%–5% gave a satisfactory reaction rate, gave a good separation between the sample containing 4 ng/ml CK-MB and non-AMI serum pool and gave low % B/T values with water.

The level of non-specific reaction diminished as the amount of matched human serum added to the mobile solid phase was increased. However, the incremental benefit obtained by adding more than 20% human serum was not great and this level of serum was used with the mobile solid phase.

The level of human gamma globulin was increased from 0.1% to 5%. The incremental benefit of adding more than 0.5% when used in conjunction with 5% BSA and 20% matched human serum was not great and level of 0.3–0.5% was used in the study.

EXAMPLE 5

This example shows the advantage of the instant invention as the radioactive tracer decays particularly when short incubation periods are used.

TABLE V

| Test Number | 1 | 2 | 3 | 4 | 5 | 6 |
|---|---|---|---|---|---|---|
| Mobile Solid-Phase Type | B | B | B | B | B | B |
| Tracer Type | E | E | E | F | F | F |
| Days in storage after preparation | 8 | 14 | 30 | 8 | 14 | 30 |
| X, ul | 200 | 200 | 200 | 200 | 200 | 200 |
| Y, ul | 200 | 200 | 200 | 200 | 200 | 200 |
| M, Min | 15 | 15 | 15 | 15 | 15 | 15 |
| V, ml | 2 | 2 | 2 | 2 | 2 | 2 |
| Z, ul | 100 | 100 | 100 | 100 | 100 | 100 |
| N, Min | 15 | 15 | 15 | 15 | 15 | 15 |
| W, ml | 2 | 2 | 2 | 2 | 2 | 2 |
| [% B/T] CK | 4.85 | 4.16 | 3.91 | 7.42 | 6.89 | 6.32 |
| [% B/T] BS | 2.67 | 2.75 | 2.76 | 3.77 | 4.07 | 4.03 |
| [% B/T] H$_2$O | 3.22 | 3.16 | 3.25 | 4.38 | 4.47 | 4.76 |
| R | 3.6 | 2.8 | 2.3 | 6.0 | 7.0 | 3.1 |

The advantage of filtering the aged tracer can be seen by comparing the R values of tests 1 and 4, 2 and 5, and 3 and 6,. The only difference in each pair was that the specific tracer of this invention was used in test numbers 4, 5, and 6.

The examples cited show that the use of the matrix of the present invention for the mobile solid-phase and tracer of the present invention allows one to achieve high accuracy even when incubation periods are shortened and the tracer ages during the use. Based on the information obtained, it was decided to use for Example 6 hereinbelow incubation periods of 15 minutes for each incubation so that the total assay could be done in less than one hour. The volumes of reagents used were 200 ul samples and calibrators, 200 ul of mobile solid phase antibody, 2 ml of "wash" buffer after each incubation and 100 ul of tracer. The mobile solid phase contained approximately 2–5% of nylon microbeads (Ab-SORB, AMF) covalently linked to goat anti-Rabbit IgG. The microbeads were suspended in a matrix of rabbit antibodies raised against CK-BB and to it were added 20% matched human serum unclarified, 0.5% human gamma globulin, 5% bovine serum albumin and 4% polyethylene glycol. The tracer was made by using affinity column purified goat antibodies raised against human CK-MM. The iodination procedure used was similar to that previously described. The iodinated material was purified over Sephadex G-25 column and high molecular weight fractions containing radioactivity were collected and pooled. This material was diluted in phosphate buffered saline, pH 7.5 containing calf serum. This dilution gave approximately 30,000 counts per minute for 100 ul of tracer. This material was allowed to stand overnight at 0°–6° C. and filtered in the presence of an anion exchange resin. Polyethylene glycol (4%) and Tween 20 (0.5%) were added to this tracer. The "wash" buffer was made of phosphate buffered saline with 0.5% BSA and 0.2% Tween 20.

EXAMPLE 6

The test method described above is represented as the "new" method. The test method which used incubation periods of 60 minutes each and which did not use the mobile solid phase matrix and tracer of this invention is represented as old method. The results obtained with new and old methods are given below. In expressing results 1 ng/ml CK-MB enzyme was assumed to give the enzymatic activity of 0.5 U/L measured at 37° C.

TABLE VI

|  | NEW | OLD |
| --- | --- | --- |
| Mobile Solid-Phase Type | C | B |
| Tracer Type | F | D |
| X, ul | 200 | 100 |
| Y, ul | 200 | 100 |
| M, Min | 15 | 60 |
| V, ml | 2 | 2 |
| Z, ul | 100 | 100 |
| N, Min | 15 | 60 |
| W, ml | 2 | 2 |
|  | Results of Test NEW | Results of Test OLD |
| A |  |  |
| Mean Value for 31 Non-AMI Patients | 0.6 ng/ml | 0.2 ng/ml |
| Standard Deviation | 0.64 | 0.54 |
| Cut-off Value for Negative Finding | 1.9 ng/ml | 1.3 ng/ml |
| B |  |  |
| Addition of 300 ng/ml CK-BB to Pooled Serum, Result Measured as CK-MB | 0.8 ng/ml | 1.4 ng/ml |
| Addition of 40,000 ng/ml CK-MM Added to Pooled Serum, Result Measured as CK-MB | 0.4 ng/ml | 2.4 ng/ml |

The addition of CK-BB and CK-MM test in "B" proves that the non-specific binding of the invention is less affected by the presence of large amounts of other CK isoenzymes than the prior art (OLD), and that in both cases the use of the instant matrix and tracer in a two-site two step sandwich technique minimizes the interference from CK-BB and CK-MM.

C. PATIENTS CONFIRMED TO HAVE AMI

Thirty-seven specimens, ranging from one to three per patient, were obtained from 16 patients having suffered AMI. The results of the two methods are correlated by the following relationship:

Value of Test NEW.=0.2+1.02 (value of test OLD).

In spite of the significantly reduced incubation time of the new method, a correlation coefficient of 0.93 was found between results of the present invention (Test NEW protocol) and Test OLD protocol, thus demonstrating that the NEW method gives comparably good results with the OLD method. However, thirteen out of the thirty-seven specimens had a CK-MB increase over the cut-off value (1.9 ng/ml) of less than 2 ng/ml by the NEW method. Only nine out of these thirteen specimens were so detected by the OLD method. Thus the NEW method correctly identified four specimens which were not identified with the prior art OLD method.

A marketable test kit may be formulated utilizing the solid phase matrix (Suspension C) and new tracer (Tracer F). The kit would comprise sufficient quantities of reagents as follows:

a. Solid-Phase Matrix—A solid-phase matrix (Suspension C) including an antiCK-BB coated bead suspension in a liquid solution including matched pooled human serum according to the disclosure hereinabove. A preservative of 0.1 percent sodium azide is added.

b. Calibrators—A series of calibrating liquids, each liquid having a differing known amount of CK-MB in pooled human serum. A preservative of 0.1 percent sodium azide is added. The pooled human serum utilized to make the calibrators is also added to the solid-phase matrix as is described hereinabove. A Control specimen having a known, stable amount of CK-MB may also be included.

c. Wash Buffer—A wash buffer comprising a phosphate buffer, pH base 7.5, having a 0.1 percent sodium azide preservative. This product is commercially available from many sources and is supplied as a convenience.

d. Tracer Solution—A tracer (Tracer F) formulated in accordance with the description hereinabove, having antiCK-MM antibody labeled with $^{125}$I.

Typically five differing calibraters are included to provide and accurate calibration curve against which patient sample results may be measured.

As will be clear to those skilled in the art, alterations and modifications may be made to the disclosed embodiments without departing from the inventive concepts thereof. The above description is therefore intended as illustrative and informative but not limiting in scope. Accordingly, it is intended that the following claims be interpreted as covering all such alterations and modifications reasonably fall within the true spirit and scope of the invention.

What is claimed is:

1. A two site immunometric sandwich assay method for the assay of creatine phospho kinase-MB(CK-MB) in human serum comprising:
    (a) reacting a serum specimen suspected of containing CK-MB with a matrix to form a first reaction solution, said matrix including;
        1. a solid-phase having an antibody to an isoenzyme selected from the group consisting of CK-MM and CK-BB bound to the surface of said solid phase; and
        2. a liquid phase surrounding said solid phase including therein a substantial component of pooled human serum;
    (b) separating the solid phase portion of said first reaction solution from the liquid portion thereof;
    (c) reacting said solid-phase portion from said first reaction solution with tracer including a labeled antibody being drawn against the remaining isoenzyme not selected in step (a) hereinabove;
    (d) separating the solid-phase portion of the second reaction solution from the liquid portion thereof;
    (e) testing said solid-phase portion from said second reaction solution to detect the tracer as an indication of the presence of CK-MB.

2. A two site immunometric sandwich assay method as recited in claim 1 and further comprising repeating steps (a)–(e) several times substituting for said serum sample in each repetition of steps (a)–(e) a calibrating sample containing a differing known amount of CK-MB whereby a calibration curve is created, and comparing the test results for said serum to said calibration curve, each said calibration sample containing a quantity of pooled human serum and said liquid phase portion of said matrix also containing a quantity of human serum drawn from the same pooled human serum as utilized in said calibrating sample.

3. A two site immunometric sandwich assay method as recited in claim 1 wherein said tracer is formulated according to the following procedure:
   (a) tagging the antibody with a radiolabel;
   (b) aging the radiolabeled antibody at a temperature of 0-6 degrees C. for at least four hours;
   (c) filtering the aged antibody.

4. The two site immunometric sandwich assay method as recited in claim 1 wherein said liquid phase includes Bovine serum albumin, Polyoxyethylenesorbitan, Polyethylene glycol and human IgG.

5. The two site immunometric sandwich assay method as recited in claim 1 wherein said human serum includes unclarified human serum.

6. The two site immunometric sandwich assay method as recited in claim 1 wherein said solid phase comprises a particulate solid phase.

7. The two site immunometric sandwich assay method as recited in claim 1 wherein said solid phase is selected from a group consisting of latex, nylon, polyacrylamide and aragose.

8. A two site immunometric sandwich assay method for the assay of creatine phospho kinase-MB(CK-MB) in human serum comprising:
   (a) reacting a serum specimen suspected of containing CK-MB with a matrix to form a first reaction solution, said matrix including;
     1. a particulate solid-phase having an antibody to CK-BB bound to the surface of said solid phase, said solid phase being selected from a group consisting of latex, nylon, polyacrylamide, polyvinylidene fluoride and agarose.
     2. a liquid phase surrounding said solid phase including therein a substantial component of pooled human serum, bovine serum albumin, Polyoxyethylenesorbitan, Polyethylene glycol and human IgG.
   (b) diluting the volume of the matrix at least 10 fold with water;
   (c) centrifuging the mixture and removing the resultant solid pellet;
   (d) resolubilizing and incubating the pellet material with a volume of a reagent including $^{125}I$ labeled antiCK-MM which has been produced as follows:
     (1) forming $^{125}I$ labeled antibodies made against human CK-MM in a species other than human;
     (2) purifying the antibody;
     (3) diluting the result of step (2) with a phosphate buffer having a pH of about 7.5;
     (4) refrigerating the result of step 3 at 0-6 degrees celsius for at least eight hours;
     (5) filtering the refrigerated result of step 4; and
     (6) adding Polyoxyethylenesorbitan, Polyethylene glycol and human IgG to the product of step (5).
   (e) diluting the volume of the mixture at least 10 fold;
   (f) centrifuging and removing the resultant solid; and
   (g) counting the radioactivity of the resultant solid; and
   (h) repeating steps (a)-(g) several times substituting for said serum sample in each repetition of steps (a)-(g) a calibrating sample containing a different known amount of CK-MB whereby a calibration curve is created, and comparing the test results for said serum to said calibration curve; each said calibration sample containing a quantity of pooled human serum and said liquid phase of said matrix also containing a quantity of human serum drawn from the same pooled human serum as utilized in said calibrating sample.

9. The process of claim 8 wherein the animal species used to raise the antibody of step (d) is different than the species used to raise the CK antibody used in step (a).

10. A reagent matrix for sandwich immunoassay testing for CK-MB isoenzyme in a test sample comprising:
    (a) a solid phase having an antibody to an isoenzyme selected from the group consisting of CK-MM and CK-BB bound to the surface of the solid phase; and
    (b) a liquid phase surrounding said solid phase including human serum as a substantial component, and wherein said human serum does not include and is not derived from said human serum sample.

11. The matrix of claim 10 wherein said liquid matrix includes bovine serum albumin, Polyoxyethylenesorbitan, Polyethylene glycol and human IgG.

12. The matrix of claim 10 wherein said human serum component of said liquid phase includes unclarified human serum.

13. The matrix of claim 10 wherein said solid phase includes a particulate solid phase.

14. The matrix of claim 11 wherein said solid phase is selected from a group consisting of latex, nylon, polyacrylamide, polyvinylidene fluoride and agarose.

15. A reagent for CK-MB immunoassay testing having a radioisotope tracer label made by the process of:
    (a) forming $^{125}I$ labeled antibodies made against human CK-MM in a species other that human;
    (b) purifying the antibody;
    (c) diluting the result of step (b);
    (d) refrigerating the result of step (c), at 0-6 degrees celsius for at least eight hours;
    (e) filtering the refrigerated the result of step (d), and
    (f) adding Polyoxyethylenesorbitan, Polyethylene glycol and human IgG to the product of step (e).

16. A test kit for the measurement of CK-MB in human serum comprising:
    a first container of a reagent matrix including an antiCK-BB coated bead suspension in a liquid solution which includes pooled human serum;
    a plurality of containers of calibrating liquids, each liquid having a differing known amount of CK-MB in pooled human serum; the pooled human serum utilized to make the calibrating liquids also being added to the matrix; and
    a container of tracer having antiCK-MM antibody labeled with $^{125}I$ in a liquid solution.

* * * * *